US011551808B2

(12) United States Patent
Colister et al.

(10) Patent No.: US 11,551,808 B2
(45) Date of Patent: Jan. 10, 2023

(54) HEALTHCARE INTEROPERABILITY ENVIRONMENT SYSTEM

(71) Applicant: Talis Clinical LLC, Streetsboro, OH (US)

(72) Inventors: Gary Colister, Hudson, OH (US); Bishoy Magdalla, Hudson, OH (US); Giuseppe Saracino, Gainsville, FL (US); William Murphy, Aurora, OH (US); Harish Lecamwasam, Scottsdale, AZ (US); Victor Lee, Twinsburg, OH (US); Matthew Schumacher, Hudson, OH (US); Kevin Gallagher, Perry, OH (US)

(73) Assignee: Talis Clinical LLC, Streetsboro, OH (US)

( * ) Notice: Subject to any disclaimer, the term of this patent is extended or adjusted under 35 U.S.C. 154(b) by 897 days.

(21) Appl. No.: 16/238,187

(22) Filed: Jan. 2, 2019

(65) Prior Publication Data
US 2019/0214128 A1 Jul. 11, 2019

Related U.S. Application Data

(60) Provisional application No. 62/612,920, filed on Jan. 2, 2018.

(51) Int. Cl.
G06F 9/44 (2018.01)
G06F 9/445 (2018.01)
(Continued)

(52) U.S. Cl.
CPC ............ G16H 40/20 (2018.01); A61B 5/002 (2013.01); A61B 5/0015 (2013.01); G16H 10/60 (2018.01);
(Continued)

(58) Field of Classification Search
CPC ...... A61B 5/0015; G16H 10/40; G16H 10/60; G16H 40/40; G16H 40/20; G16H 40/67;
(Continued)

(56) References Cited

U.S. PATENT DOCUMENTS 5,954,666 A 9/1999 Snell
6,229,536 B1 5/2001 Alexander et al.
(Continued)

FOREIGN PATENT DOCUMENTS

EP 3839960 A1 6/2021
WO 2021002847 A1 1/2021
WO 2021067485 A1 4/2021

OTHER PUBLICATIONS

Tao et al., A Hybrid Transaction Processing and Data Analysis Framework: A Use Case Study for Multi-Source Healthcare Data Management, 5 pages (Year: 2016).*
(Continued)

Primary Examiner — Thuy Dao
(74) Attorney, Agent, or Firm — Brian P. Harrod; George W. Moxon, II

(57) ABSTRACT

The invention concerns an Interoperability Environment comprising: a core software engine comprising means to collect and transfer electronic data from any number of sources including medical devices, clinical information systems, hospital information systems, a means to apply rules to improve compliance with hospital approved protocols, standards and guidances, a means to update all subsystems using any given parameter when the parameter is updated in the official recognized source of truth for that parameter, a means to populate the CIS with all required patient information, while at the same time maintaining all quality and process control data in a format supporting advanced analytics separate from the CIS data, a means to communicate notifications to any number of remote electronic devices
(Continued)

without limitation of platform and comprising a hardware eco system comprising means to collect, translate, store and send electronic data to the core software engine for any electronic source via communication methods including but not limited to LAN, Serial, Wi Fi, Wireless, etc.

19 Claims, 7 Drawing Sheets

(51) Int. Cl.
| | |
|---|---|
| G06F 11/34 | (2006.01) |
| G06F 9/46 | (2006.01) |
| G06F 11/00 | (2006.01) |
| G16H 40/20 | (2018.01) |
| G16H 10/60 | (2018.01) |
| A61B 5/00 | (2006.01) |
| G16H 40/40 | (2018.01) |
| H04L 67/125 | (2022.01) |
| H04L 67/50 | (2022.01) |
| H04L 67/565 | (2022.01) |
| G16H 10/40 | (2018.01) |
| A61B 5/145 | (2006.01) |
| H04L 69/08 | (2022.01) |

(52) U.S. Cl.
CPC ........... G16H 40/40 (2018.01); H04L 67/125 (2013.01); H04L 67/535 (2022.05); H04L 67/565 (2022.05); *A61B 5/14542* (2013.01); *A61B 5/412* (2013.01); *A61B 5/4836* (2013.01); *A61B 5/7275* (2013.01); *G16H 10/40* (2018.01); *H04L 69/08* (2013.01)

(58) Field of Classification Search
CPC .. G16H 40/63; G16H 50/20; H04L 29/06068; G06N 5/046; G06N 5/025; G06F 9/542; G06Q 10/087; G06Q 30/0603; G06Q 10/06; G06Q 10/10; G06Q 40/02
See application file for complete search history.

(56) References Cited

U.S. PATENT DOCUMENTS

| | | | |
|---|---|---|---|
| 6,364,834 B1 | 4/2002 | Reuss et al. | |
| 6,553,436 B2 | 4/2003 | Ando et al. | |
| 6,559,868 B2 | 5/2003 | Alexander et al. | |
| 7,315,825 B2 | 1/2008 | Rosenfeld | |
| 7,467,093 B1 | 12/2008 | Newton et al. | |
| 8,000,937 B2 | 8/2011 | Zeng et al. | |
| 8,149,131 B2 | 4/2012 | Blomquist | |
| 8,229,760 B2 | 7/2012 | Hasan et al. | |
| 8,291,337 B2 | 10/2012 | Gannin et al. | |
| 8,310,336 B2 | 11/2012 | Muhsin et al. | |
| 8,553,036 B2 | 10/2013 | Taylor et al. | |
| 8,660,860 B2 | 2/2014 | Wehba et al. | |
| 8,674,837 B2 | 3/2014 | Gilham et al. | |
| 8,730,243 B2 | 5/2014 | Wenholz et al. | |
| 8,732,095 B2* | 5/2014 | Cornford | G06Q 10/06 706/12 |
| 8,892,171 B2 | 11/2014 | Ross et al. | |
| 8,990,722 B2 | 3/2015 | Gannon et al. | |
| 9,095,274 B2 | 8/2015 | Fein et al. | |
| 9,179,852 B2 | 11/2015 | Audet et al. | |
| 9,183,351 B2* | 11/2015 | Shusterman | G16H 40/67 |
| 9,393,366 B2 | 7/2016 | Gannon et al. | |
| 9,400,874 B2 | 7/2016 | Powell et al. | |
| 9,927,943 B2 | 3/2018 | Gannon et al. | |
| 10,255,408 B2 | 4/2019 | Blomquist | |
| 10,332,639 B2* | 6/2019 | Smurro | H04N 7/147 |
| 10,354,751 B1 | 7/2019 | McNair | |
| 10,657,222 B2 | 5/2020 | Chan et al. | |
| 11,030,872 B2 | 6/2021 | Chan et al. | |
| 11,031,129 B2 | 6/2021 | Zaleski | |
| 2004/0054294 A1 | 3/2004 | Ramseth | |
| 2005/0159666 A1 | 7/2005 | Pearce et al. | |
| 2005/0171815 A1 | 8/2005 | Vanderveen | |
| 2007/0179806 A1 | 8/2007 | Knowlton et al. | |
| 2008/0097914 A1 | 4/2008 | Dicks et al. | |
| 2008/0316045 A1 | 12/2008 | Sriharto et al. | |
| 2011/0227739 A1 | 9/2011 | Gillham et al. | |
| 2012/0035957 A1 | 2/2012 | Hanz et al. | |
| 2012/0278099 A1 | 11/2012 | Kelly et al. | |
| 2014/0046674 A1 | 2/2014 | Rosenfeld et al. | |
| 2014/0142963 A1 | 5/2014 | Hill et al. | |
| 2014/0222446 A1 | 8/2014 | Ash et al. | |
| 2014/0249855 A1 | 9/2014 | Moore | |
| 2014/0266787 A1 | 9/2014 | Tran | |
| 2015/0025329 A1 | 1/2015 | Amarasingham et al. | |
| 2016/0246943 A1 | 8/2016 | Lake et al. | |
| 2017/0140108 A1 | 5/2017 | Lee et al. | |
| 2017/0372037 A1 | 12/2017 | Muecke et al. | |
| 2020/0035366 A1 | 1/2020 | Gummireddy et al. | |
| 2020/0227148 A1 | 7/2020 | Cohen et al. | |
| 2020/0359913 A1 | 11/2020 | Ghodrati et al. | |
| 2020/0394334 A1 | 12/2020 | Bulut et al. | |
| 2021/0065889 A1 | 3/2021 | Page | |
| 2021/0077035 A1 | 3/2021 | Kayser et al. | |
| 2021/0141786 A1 | 5/2021 | Gubau I Forne et al. | |
| 2021/0151145 A1 | 5/2021 | Dunn et al. | |
| 2021/0151178 A1 | 5/2021 | Singh et al. | |
| 2021/0202086 A1 | 7/2021 | Cherdak | |
| 2021/0225505 A1 | 7/2021 | Khare et al. | |
| 2021/0233628 A1 | 7/2021 | Rentas et al. | |

OTHER PUBLICATIONS

Rahman et al., A Location-Based Mobile Crowdsensing Framework Supporting a Massive Ad Hoc Social Network Environment, 10 pages (Year: 2017).*

* cited by examiner

HEALTHCARE INTEROPERABILITY ENVIRONMENT SYSTEM

BACKGROUND OF THE INVENTION

The present invention is directed to an improved interoperability environment, such as for example patient care, healthcare clinics and hospitals, in which the parameters that guide the healthcare are updated by a truth configuration engine to create an officially recognized source of truth for those parameters.

Hospitals and Health Care Facilities make extensive efforts to establish quality metrics to demonstrate their commitment to establish a continuous spiral of improved patient care outcomes and regulatory compliance. The motivations for these efforts are almost endless. The current infrastructure available to drive this objective is described below.

Hospitals and Health Care Facilities utilize multiple software systems. These subsystems are required to support specific functional departments or care areas of the health care facility. The various subsystems or Specialty Focused Software Systems (SFSS) are primarily used by that specific functional department. Each SFSS and its users assume that the SFSS is the source of truth for all parameters defined in that software tool. Examples of SFSS include but are not limited to: Electronic Medical Records (EMR), Admission, Discharge and Transfer (ADT), Anesthesia Information Management System (AIMS), Electronic Medication Administration Record (EMAR), Pharmacy, Drug Dispensing, Purchasing, Billing, Infection Control, Lab, etc. These systems are generally designed to support a generically acceptable approach to the required documentation and data collection. Therefore, the SFSS have fairly rigid workflow requirements with limited support of customization. Additionally, due to the data management approach, altering a SFSS configuration after initial go live is limited.

Hospitals and Health Care facilities use medical devices, these medical devices either monitor well defined vital signs, deliver user programmed medical therapy or a combination of the two. Almost all electronic medical devices designed and introduced into the market within the last 25 years have access ports or some means to send electronic data out. The available data may include information such as: user programming details, basic operation data, details involving alerts and alarm conditions, details of the therapy delivered and when applicable patient monitored vital signs. Currently the data regarding the patient monitored vital signs may be forwarded to the EMR to populate the patient care record. However, while the data is available it is not routinely sent and stored in a storage location in a manner supportive of basic process control tools to drive fact based process improvements.

Hospitals and Health Care Facilities use, in addition to the SFSS identified above, various hardware and/or software solutions that may collect, translate and transfer data from medical devices to desired storage targets. They also use hardware and/or software solutions that support specific protocol work flows and in some occasions, the hardware and/or software solutions may support point of care workstations, remote display screens, remote access workstations, and notification features, including notifications to mobile devices. The focus of these tools is to improve compliance with hospital defined protocols and required documentation. Some remote view screens are intended as supervision or process tools to monitor the active protocols and/or patient care remotely.

Physiological Based Closed Loop Controlled Medical Devices focus on the interoperability between various patient monitoring medical devices with medical devices providing medical therapy to the patient. The use of the term "vital signs" can be used to distinguish between the basic vital signs taken at the point of care and the more generic term physiological parameters which includes both vital signs as well as any number of other patient specific details relevant to the optimum patient care such as Lab Results, patient specific medical history (including known physiological conditions which may lead to preventable complications, such as drug allergies or sleep apnea), images, assessments against commonly accepted care guidance checklist such as Sepsis or other patient risk assessment tools.

The current Physiological Based Closed Loop Controlled Medical Devices appear to focus on identifying the means to allow the patient monitoring medical devices to communicate with the medical devices providing patient therapy to appropriately adjust the therapy being provided. Therefore, the current devices and systems appear to assume that only vital signs collected at the point of care are required to provide clinically proven algorithms all the information required to make the appropriate decision to adjust the medical device provided therapy. This approach limits the full potential of a device interoperability infrastructure. If the interoperability capabilities of the system were expanded to include all available (not limited to medical devices) patient specific details that are applicable to developing and controlling the optimum patient care outcome, then the true goal of Physiological Based Closed Loop Controlled Medical Devices can be advanced in a meaningful way.

Thus there is a need to provide a meaningful tool that recognizes the current knowledge base of advanced process control tools at any specific hospital, with the capability of being modified as the hospital gains new knowledge. This would require expanding the system capabilities substantially by expanding the scope of interoperability.

SUMMARY OF THE INVENTION

The invention concerns an Interoperability Environment comprising: at least one hardware eco system comprising a rules engine to collect, translate, store and send electronic data to the core software engine for any electronic source via communication methods including but not limited to LAN, Serial, Wi Fi, Wireless, etc. a core software engine comprises means to collect and transfer electronic data from any number of sources including medical devices, clinical information systems, hospital information systems, a rules engine to apply rules to improve compliance with hospital approved protocols, standards and guidances, a rules engine to apply rules to update all subsystems using any given parameter when the parameter is updated in the official recognized source of truth for that parameter, a rules engine to apply rules to populate the CIS with all required patient information, a rules engine to apply the rules to maintain all quality and process control data in a format supporting advanced analytics separate from the CIS data, a rules engine to provide a means to communicate notifications to any number of remote electronic devices without limitation of platform, rules engines to support data analysis including failure investigation and process control and machine learning tools, rules engines providing a means to improve adherence to medical practitioner directed patient care, and rules engine to provide two-way communication with electronic devices including medical devices.

BRIEF DESCRIPTION OF DRAWINGS

The foregoing and other features and advantages of the present invention will become apparent to those skilled in the art to which the present invention relates upon reading the following description with reference to the accompanying drawings, in which.

DETAILED DESCRIPTION OF THE INVENTION

Figure 1:
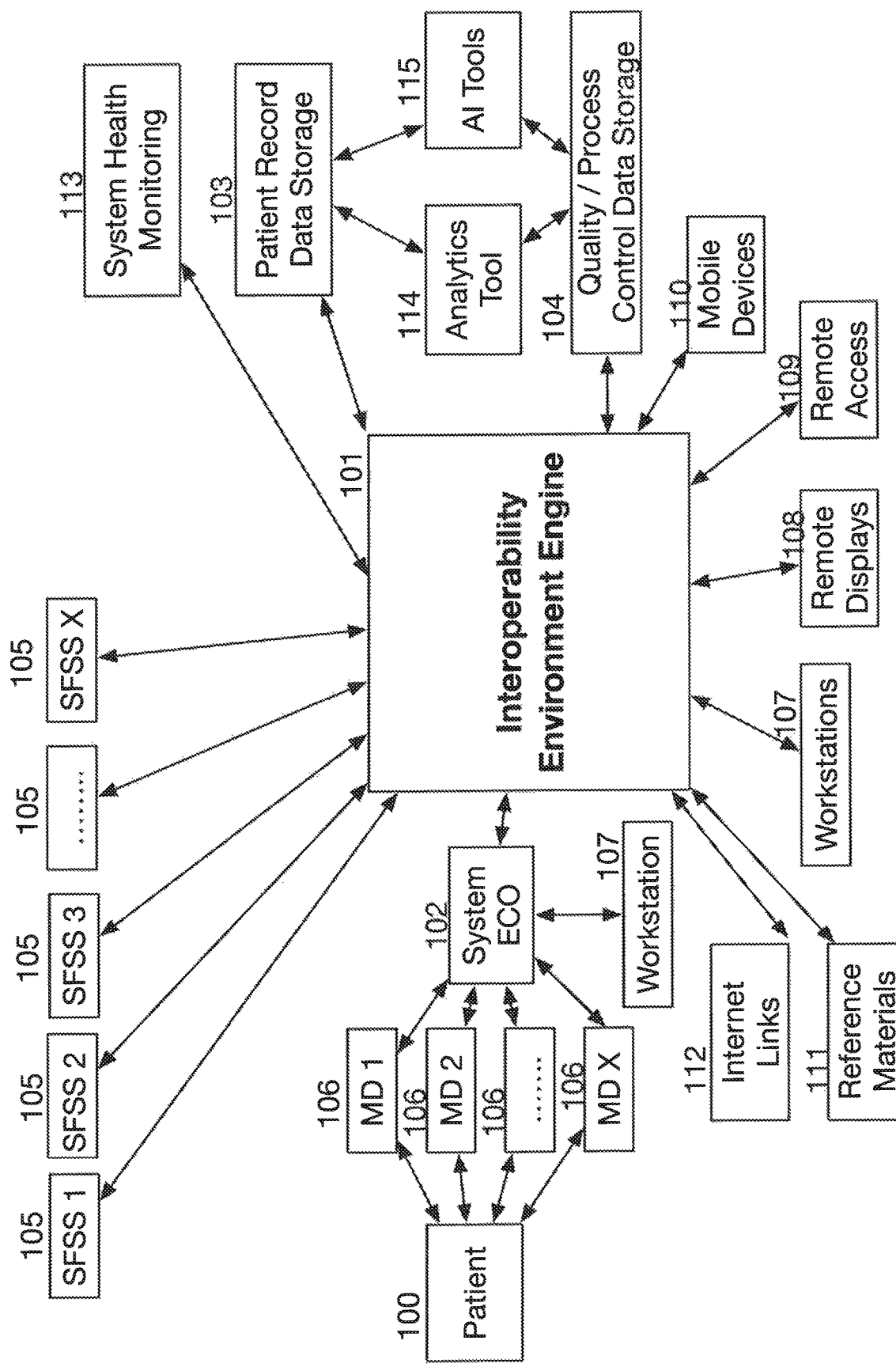
FIG. 1 is a flow diagram of a global view of an Interoperability Environment showing the various communication sources and targets.

The present invention is directed to a Global Interoperability Environment, which changes the paradigms currently associated with device interoperability which includes a telecommunications network, at least one monitoring station comprising monitoring equipment wherein the monitoring equipment comprises instructions for retrieving data elements and for sending the monitored data elements to any number of rules engines, where the rues engine (s) comprises instructions for receiving monitored data elements from patients, accessing patient data elements indicative of a medical conditions associated with each of the patients, a patient database containing information concerning the medical condition, history, and status of each of the patients, a truth configuration engine comprising a means to identify when a data element, shared by more than one electronic systems, is changed, once changed provide means to update the parameter in each connected electronic system, using the parameter, with the new value, a means to defer the update of the parameter based on defined rules when applicable. The present invention provides a meaningful tool, that recognizes the current knowledge base of advanced process control tools at any specific hospital with the capability of being modified as the hospital gains new knowledge.

The present invention uses a telecommunications network to facilitate rules-based care of patients receiving care in a healthcare location. A healthcare location may be a hospital, surgery center, remote clinic, a doctor's office, a field hospital, a disaster aid station, a patient transport vehicle and similar care facilities.

The invention concerns an Interoperability Environment comprising: at least one hardware eco system comprising a rules engine to collect, translate, store and send electronic data to the core software engine for any electronic source via communication methods including but not limited to LAN, Serial, Wi Fi, Wireless, etc. a core software engine comprises means to collect and transfer electronic data from any number of sources including medical devices, clinical information systems, hospital information systems, a rules engine to apply rules to improve compliance with hospital approved protocols, standards and guidances, a rules engine to apply rules to update all subsystems using any given parameter when the parameter is updated in the official recognized source of truth for that parameter, a rules engine to apply rules to populate the CIS with all required patient information, a rules engine to apply the rules to maintain all quality and process control data in a format supporting advanced analytics separate from the CIS data, a rules engine to provide a means to communicate notifications to any number of remote electronic devices without limitation of platform, rules engines to support data analysis including failure investigation and process control and machine learning tools, rules engines providing a means to improve adherence to medical practitioner directed patient care, and rules engine to provide two-way communication with electronic devices including medical devices.

The ECO system hardware acquires data elements from medical devices including patient monitors and transmits the data over a network to data storage, identified targets, individuals requiring notification, remote dashboards, remote mobile communication devices, remote monitoring locations. The collected data comprises physiological data elements, video data elements, audio data elements, manually entered patient evaluations, drug delivery, incision time and location, blood product delivery, lab results, admitting evaluation results, post-operative assessments, I/O data, etc. The Interoperability Environment also accesses other data relating to the condition of a patient. By way of illustration and not as limitation, the Interoperability Environment has access to data relating to personal information about the patient, medical history (illnesses, injuries, surgeries, allergies, medications, etc.), admissions information (symptoms, physiological data, time of admission, observations of admitting caregiver), treatment, lab data, test reports (radiology reports and microbiology reports for example), physician's notes, a patient's diagnosis, prescriptions, history, condition, laboratory results and other health-relevant data (collectively "patient data") to the extent available from the healthcare IT network. The data collected over the network, that is, the monitoring data and the patient data, is collectively referred to as "assessment data."

The present invention changes the paradigms currently associated with the current specialty focused software systems and medical device interoperability approaches. The first paradigm shift is the utilization of an agnostic approach to communications between data sources and data targets. The present invention allows the hospital to utilize any number of suppliers and/or device models within the interoperability environment. This eliminates the need to buy new equipment or software just to achieve interoperability. The next paradigm shift is the expansion medical device interoperability from interoperability between two medical devices at the point of patient care to the realization that effective patient assessment requires the ability to access all relevant patient data from all applicable sources as discussed above. This paradigm shift expands the individual practitioners' and the healthcare facility/systems' ability include the use of more advanced process tools and optimization of workflow compliance, driving a continuous spiral of improvement to patient care outcome and regulatory compliance. The expansion these paradigms forces a realization that until the true source of truth for all applicable parameters are known and utilized everywhere appropriate, the spiral of improvement is slowed, if not stopped. This potential to shift the paradigms is the result of the design team's experience, that new knowledge is gained over time and often results in significant changes to assumed sources of truth, proper workflow, required activities, and changes in documentation required to support the new knowledge. There is a significant realization that there are at least five basic roles of any data system (1) document all required patient care and patient response/outcome data accurately and completely, (2) provide the ability to collect process control data in an ever-changing environment, (3) optimize the efficiency of the organization, (4) support advanced analytic tools and artificial intelligence tools, and (5) rapidly communicate the relevant information to the individual(s), who need the information. To meet these roles effectively, the present invention provides a means to store accurately, timely and completely all relevant data regarding patient care and patient response/outcome. At the same time, the invention stores all applicable process and quality data accurately, timely and completely in a separate storage. The storage format is compatible with advance analytic and artificial intelligence tools. The present invention allows the flexibility of collecting process control data only to find that it is either not beneficial or not beneficial without additional information, and thus places the ultimate focus on the current level of the hospital knowledge of its processes, defined protocols, guidance standards, reimbursement and regulatory requirements in its journey to improve patient care outcome, while supporting any number of changes required to gain new meaningful knowledge.

The current physiological based closed loop controlled medical devices focus on the interoperability between various patient monitoring medical devices with medical devices providing medical therapy to the patient. The term, vital signs is used to distinguish between the basic vital signs taken at the point of care and the more generic term physiological parameters which includes both vital signs as well as any number of other patient specific details relevant to the optimum patient care such as lab results, patient specific medical history, including known physiological conditions which may lead to preventable complications, such as drug allergies or sleep apnea), images, assessments against commonly accepted care guidance checklist such as Sepsis or other patient risk assessment tools.

The present invention focuses on identifying the means to allow the patient monitoring medical devices to communicate with the medical devices providing patient therapy to appropriately adjust the therapy being provided. Current systems assume that only vital signs collected at the point of care are required to provide clinically proven algorisms all the information required to make the appropriate decision to adjust the medical device provided therapy, which limits the full potential of a device interoperability infrastructure. The present invention expands the capabilities of the system to include all available, but not limited to, medical devices, patient specific details that are applicable to developing and controlling the optimum patient care outcome.

FIG. 1 is a block diagram of the global Interoperability Environment. At the center of FIG. 1 is the Interoperability Environment Engine 101, referred to as the engine. This is to symbolize that it is the core communication tool to ensure timely and accurate communication between the various sources and targets of the data being collected and shared in the global environment. As noted by the two-way arrows, the present invention also supports communication between any number of locations with connections to the Interoperability engine.

The Interoperability Environment is also composed of an ECO system 102. The ECO System is composed of any number of hardware options, utilizing various operating systems such as Linux, Windows, and MacOS. The ECO system resides in close proximity of the electronic devices, including electronic medical devices (or EMD) 106, talking with the ECO System, via any number of communication channels including LAN, serial, Wi Fi, wireless, etc. The ECO system is utilized as the conduit between the medical devices and the engine to collect, translate and transfer electronic data to the engine for processing to the proper storage locations or specific data targets.

The Interoperability Environment is also composed of one or more data repositories to store all data collected prior to sending the data to any target location. For example, the data can come from the patient 100, electronic medical devices 102, work stations 103, patient record data storage 106, remote displays 108, remote access devices 109, mobile devices 110, reference materials 111, internet links 112, and the like. The engine tracks each data field based on a start date and end date of the parameter being collected. When combined with the engine time stamping and data collecting, the Interoperability Environment is capable of supporting data analysis of individual parameters as well as interactions with other parameters. Patient Record Data Storage 103 contains all required patient care data collected and stored by the engine. It may interact with available analytics tool 114 and/or artificial intelligence (AI) tools 115, as needed. Quality/Process Control Data Storage 104, which is stored separate from the Patient Care data, contains all data collected to support quality and process control efforts.

Figure 2:
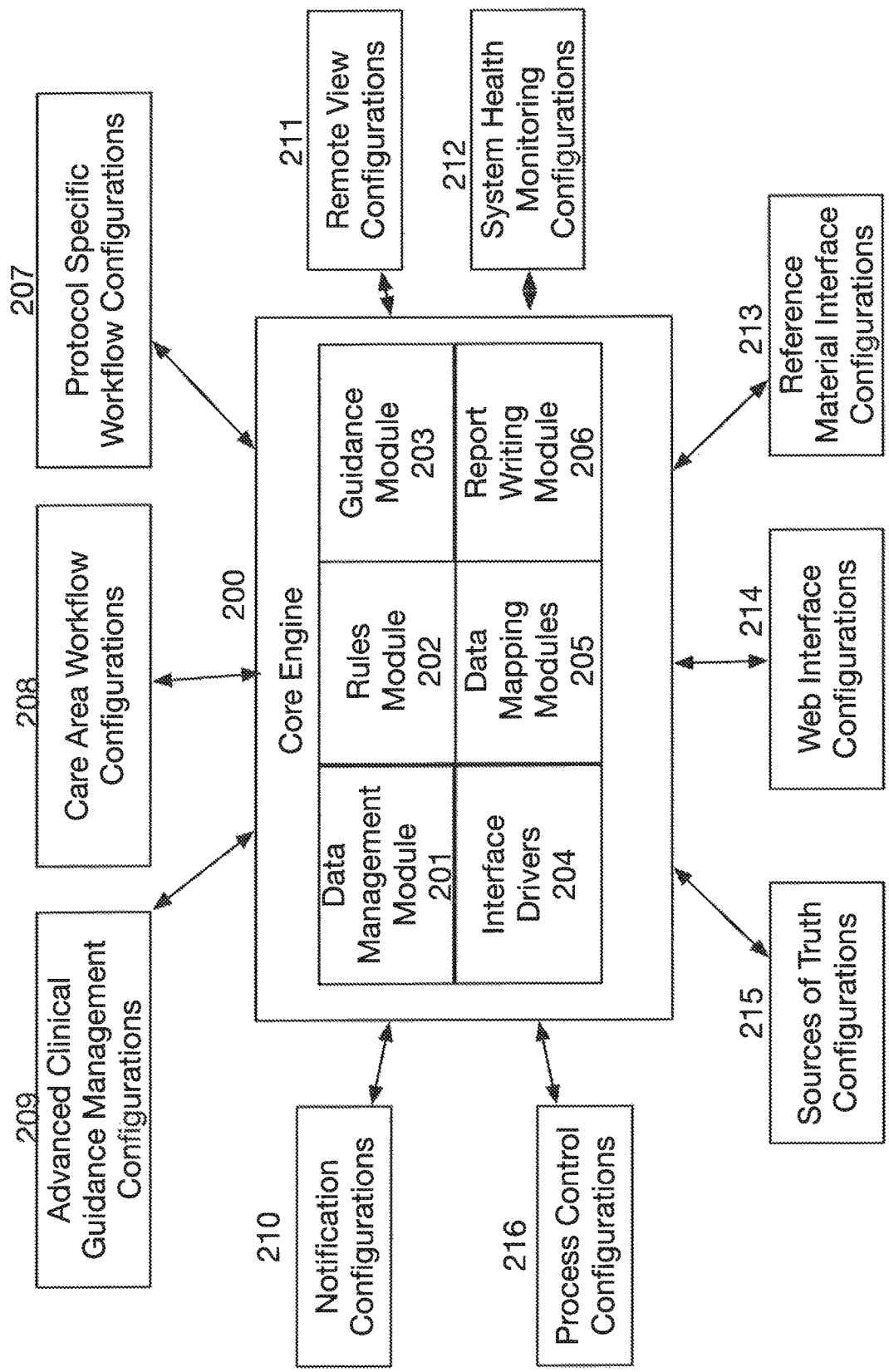
FIG. 2 is a flow diagram of the interoperability environment engine and configurations showing the modules and examples of supported activity configurations capable of being supported without modification to the engine.

The engine is the tool that manages the data collection and storage, adherence to applicable rules defined by the Hospital, management and tracking of the guidance standards and rules defined by the hospital, communication with various data format languages, and report writing capabilities. FIG. 2 is a block diagram of the interoperability environment engine modules and examples of functionality specific configurations. The details of the specific roles and responsibilities of the modules within the engine are discussed below.

For example, Specialty Focused Software System (SFSS 1) 105 is the originating source for a parameter, which will be referred to as "AB", which is used by, for example, SFSS 1 (originating source), SFSS 4 or SFSS X, patient's Sepsis Checklist, and the EMR. When the parameter AB is updated in SFSS 1 (originating source), the parameter is immediately updated in SFSS1, SFSS4 and SFSSX, Patient's Sepsis Checklist and the EMR. If defined by the hospital the parameter update may be scheduled to a later time as defined per hospital rules for any number of locations.

The Data Management Module 201 provides the means to provide a means to support unlimited expansion and changes, a means to provide a data audit trail, a means to link data collected to the reports utilized when the data was collected, and a means to support even significantly large changes such as the conversion from one EMR platform to another, without losing the context of the data collected under the old EMR. This results in many fields no longer being populated and new fields being initiated.

The Rules Module 202 provides the means to apply and monitor compliance to the rules associated with specific well-defined protocols and workflow. The rules module in conjunction with the data management tool provide a means to manage, apply and monitor the control of the source of truth across the interoperability environment.

The Guidance Module 203 provides means to apply and monitor compliance to any number of guidance standards or requests, while the Data Mapping Module 204 provides a means to ensure that incoming and outgoing data is populated into the proper location(s).

The Report Writing Module 205 provides the means to generate reports in both electronic and printed format. The report writing module provides a means to provide customized user interface screens supportive of hospital rules, guidance standards, workflow, prompts, alerts, notifications, etc. The Interface Drivers 206 utilizes any number of source or target specific communications drivers to provide a means to communicate with any number of recognized electronic data formats.

The engine also utilizes any number of functionality specific configurations. FIG. 2 provides examples of these functionality specific configurations. As part of the implementation process the functionality specific details need to be configured. Examples of potential functionality specific configurations are described below.

The Protocol Specific Workflow Configurations 207 provide the means to provide protocol specific interactive workflow screens to improve compliance with protocol and documentation requirements, while providing prompts and alerts when required activities are needed or have not been completed. The Care Area Workflow Configurations 208 provide the means to monitor scheduled activities, provide prompts to improve compliance with hospital protocols that are time sensitive such as IV set change outs. Care Area workflow configurations may utilize both interactive workflow screens and remote view screens at the care area central desk.

Advanced Clinical Guidance (ACG) Management Configurations 209 provide the means to provide guidance specific interactive workflow screens and remote view screens to improve compliance with the guidance and documentation requirements, while providing prompts, alerts and notifications when required activities are needed or have not been completed. The ACG configuration process controls are defined by the hospital or individual practitioner based on authority levels granted to individuals. These process limits may be altered easily as new knowledge is acquired to justify changes to patient care protocol limits.

The Notification Configurations 210 provide the means to notify, identified individuals based on hospital rules and guidance standards and/or authorized medical practitioner requests. Remote View Configurations 211 provide a means to display any number of variations of information as determined appropriate for the remote view location. Remote view configurations provide the ability to request additional details for specific icons on the remote view. The feature may be described as an information dive down capability. No patient ID information is viewable in these views.

The Reference Material Interface Configurations 213 provide the ability to link to useful reference materials 111 prior to or during protocols, and the Web Interface Configurations 214 may provide the ability to utilize internet links 112 to access useful web based information prior to or during protocols. Web interface configurations may provide web access to remote view information, or if practitioner is authorized more patient specific details.

The System Health Monitoring 212 configurations provide a means for the company to support Interoperability Environment by utilizing a remote view of the system components (including but not limited to: communication links, power source status, latest interaction, settings, etc. of the ECO system, electrical devices including medical devices, IT network, etc.) to quickly assess potential issues prior to a hospital detecting the issue. The system is also utilized when a support call is received, the system allows the support team to see any number of details regarding the operation or status of the various electronic devices including medical devices, connected to the Interoperability Environment Engine. No patient ID information is viewable in this tool.

Source of Truth Configurations 215 provide a means to manage parameter values across any number locations utilizing the same parameter. Management implies the following here: hospital identifies the recognized source of truth, every software database interacting with the Interoperability Environment Engine that uses the specific parameter is updated when the parameter in the identified source of truth is changed. The update may be immediate or delayed based on the hospital-identified rules for each software database. These configurations may be modified or changed as new knowledge is gained.

Process Control Configurations 216 provide a means to collect and manage the hospital identified required process control data to collect and store. Once stored advanced analytical analysis supported by process control tools such as Hazard Analysis and Critical Control Point may be used to identify the critical steps and the control requirements determined for any process. Again because of the configuration approach of the Interoperability system, as process knowledge is gained modifications may be easily implemented based on hospital authorization protocols.

Figure 3:
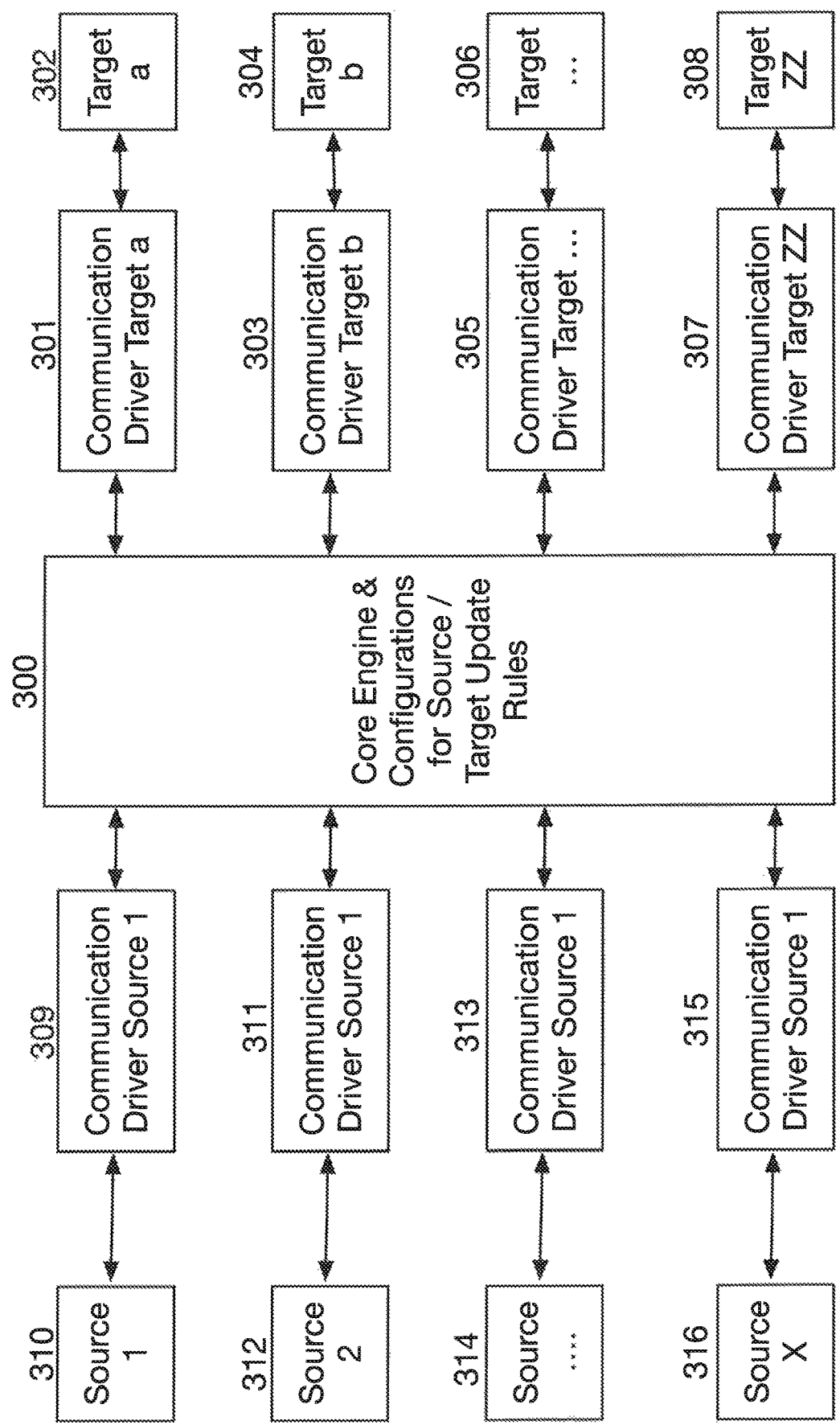
FIG. 3 is a flow diagram of the system of the present invention showing that the system is agnostic to target and source communications.

FIG. 3 illustrates that the system of the present invention is agnostic as to target and source communications requirements. The system is uniquely configured to utilize communication driver configurations specifically configured for each source or target electronic device including medical devices. Any source may update multiple targets and the flow paths may be two directional. Further, the targets of one parameter may be a source of other parameters. This agnostic approach eliminates the need for standardized communication platforms. Stated differently, the agnostic approach allows the customer to utilize existing electrical devices including medical devices or to select devices based on its performance features rather than its compatibility with another device.

For example, an admission discharge and transfer system (ADT) is used to schedule surgeries in the operating rooms. Once the patient is identified and recorded in the system, the system accesses the ADT to confirm the patient is scheduled and compatible with the ADT record.

To verify the patient is the correct patient for the case, several items must be compared between the ADT record and the patient ID band. These include: patient name and patient number. Additionally, information from the ADT and Patient ID will be utilized to populate the anesthesia record, including: Case #, patient name, Patient number, assigned anesthesiologist, attending surgeon, type of protocol, and the like. Several SFSS utilize many of these data parameters. To adequately ensure that the patient, being evaluated prior to treatment is the correct patient for the planned treatment, the various subsystems must be in full agreement. When discrepancies are identified, patient treatment is delayed until the discrepancies are resolved.

Patient histories from the Electronic Medical Record (EMR) are required to be documented in the Anesthesia record. Therefore, the system obtains the required information from the EMR and populates the Anesthesia Record with the required information. More detailed listing of information pulled from the EMR to populate the anesthesia record include: Patient name and number, relevant patient history such as allergies, heart condition, known physiological conditions which may increase the complexity of the procedure or impact the care of the patient. Without the accurate and effective electronic communication between these record systems, the duplicated entries of the same information by multiple individuals increases the potential for discrepancies between the subsystems even when both are electronic records. With manual records the potential for discrepancies is even greater, with decreased confidence that the discrepancies will be detected.

Vital signs from a medical device are required to be recorded at specified time frames in the anesthesia record. The system obtains the vital signs from the medical device and sends the required information into the patient record(s). This could be the anesthesia record and the Electronic Medical Record system at the same time. More detailed listing of information pulled from the EMR to populate the anesthesia record include: Patient name and number, relevant patient history such as allergies, heart condition, known physiological conditions which may increase the complexity of the procedure or impact the care of the patient. Without the electronic retrieval of vitals sign values from patient monitors, the anesthesia record is updated with manual entries. The accuracy of these entries may be difficult if not impossible to confirm if the patient monitor history is reviewed in detail and compared to the numeric values manually entered into the record. This is compounded when the patient monitor internal clock records are not synchronized with the clocks in the operating room.

Key patient data collected during the procedure must be sent to the EMR and entered into the appropriate location to ensure that the values are accurately recorded as part of the case. Examples include: attending practitioner, specific practitioner responsible for performing a specific activity during the case, vital signs collected from the active patient monitors, manually enter values as required by the procedure protocol.

The information from the anesthesia record including, drugs delivered, disposable medical devices, services provided, level of medical practitioner charged for the service, etc. are pushed to the billing system to generate accurate and timely billing. Again this information must be accurately sent to the billing system in a manner that ensures all required information is assigned to the correct patient, case, and the like.

Figure 4:
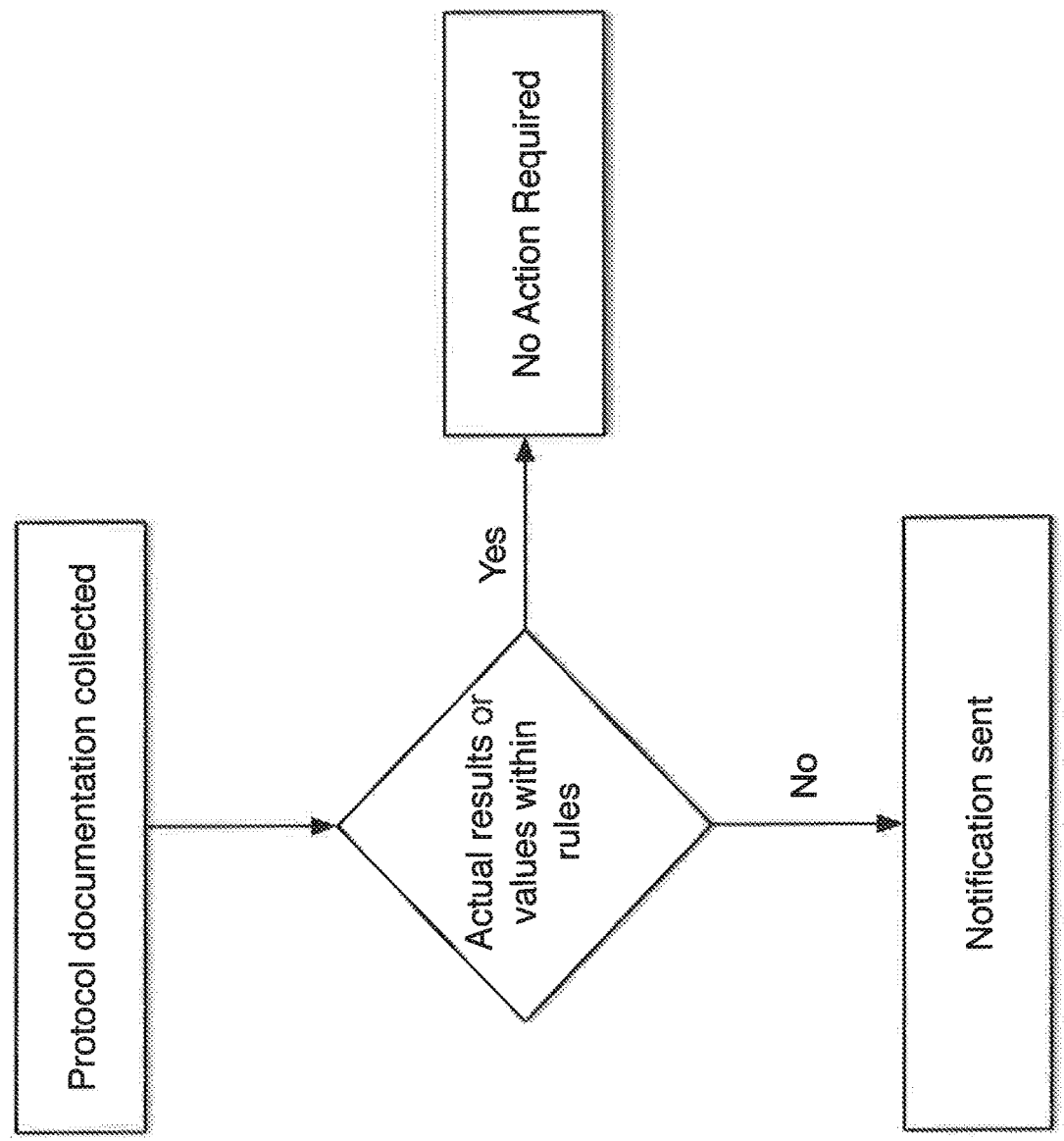
FIG. 4 illustrates the flow of a decision support algorithm in accordance with the present invention.

All protocol and notification rules are defined by the medical facility. The system is configured to apply these rules as defined. FIG. 4 shows an algorithm in which a guidance is reviewed. An example would involve an antibiotic delivery where an antibiotic is required to be given prior to the start of the procedure. The user attempts to start the procedure. However, the delivery of the antibiotic has not been documented. The workflow screen will display the notification that Antibiotic has not been given. In another example, a specific drug is required to be manually delivered every 30 minutes during a procedure. The delivery must be manually entered. If the required information is not entered when required, the system prompts the practitioner to take the required action and document the action. If a manually entered vital sign must be recorded every 15 minutes and it has been more than 15 minutes, the workflow screen will display the notification to the user that the vital sign has not been entered. If the medical facility defined protocol vital sign limits have been exceeded, the workflow screen will display the notification to the user that the defined limit has been exceeded and the patient response is not within acceptable ranges.

Figure 5:
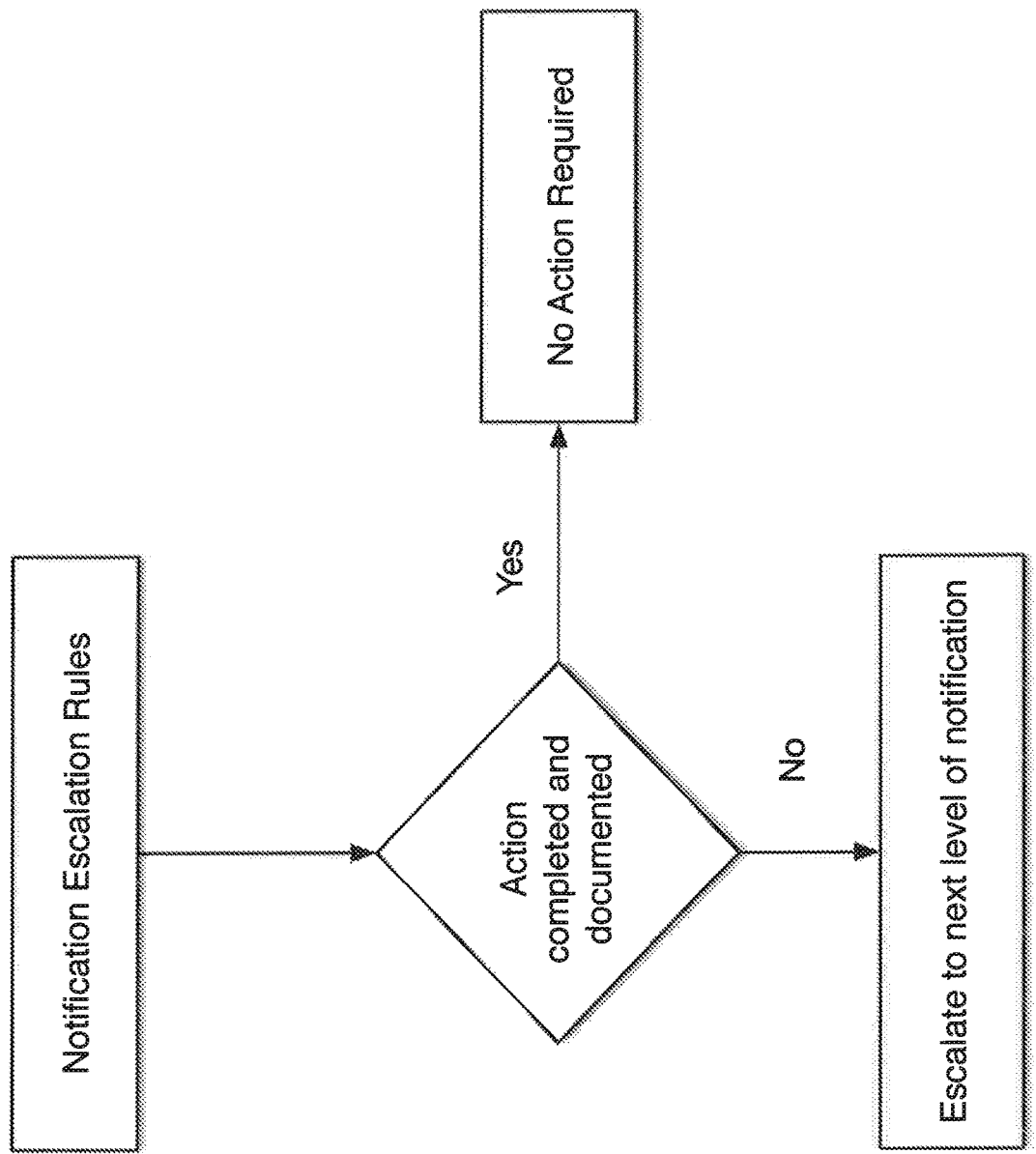
FIG. 5 illustrates the flow of a further decision support algorithm in accordance with the present invention.

The protocol reflected in FIG. 4 will also flow in the predictive risk management and response tools of FIG. 5 where if escalation is required by the medical facility and the required action is not performed and documented within the allotted time, the system may be set up to escalate the notification to another responsible individual to take the appropriate actions. The escalation process continues until the required action has been taken and documented or until all identified responsible individuals have been identified.

Figure 6:
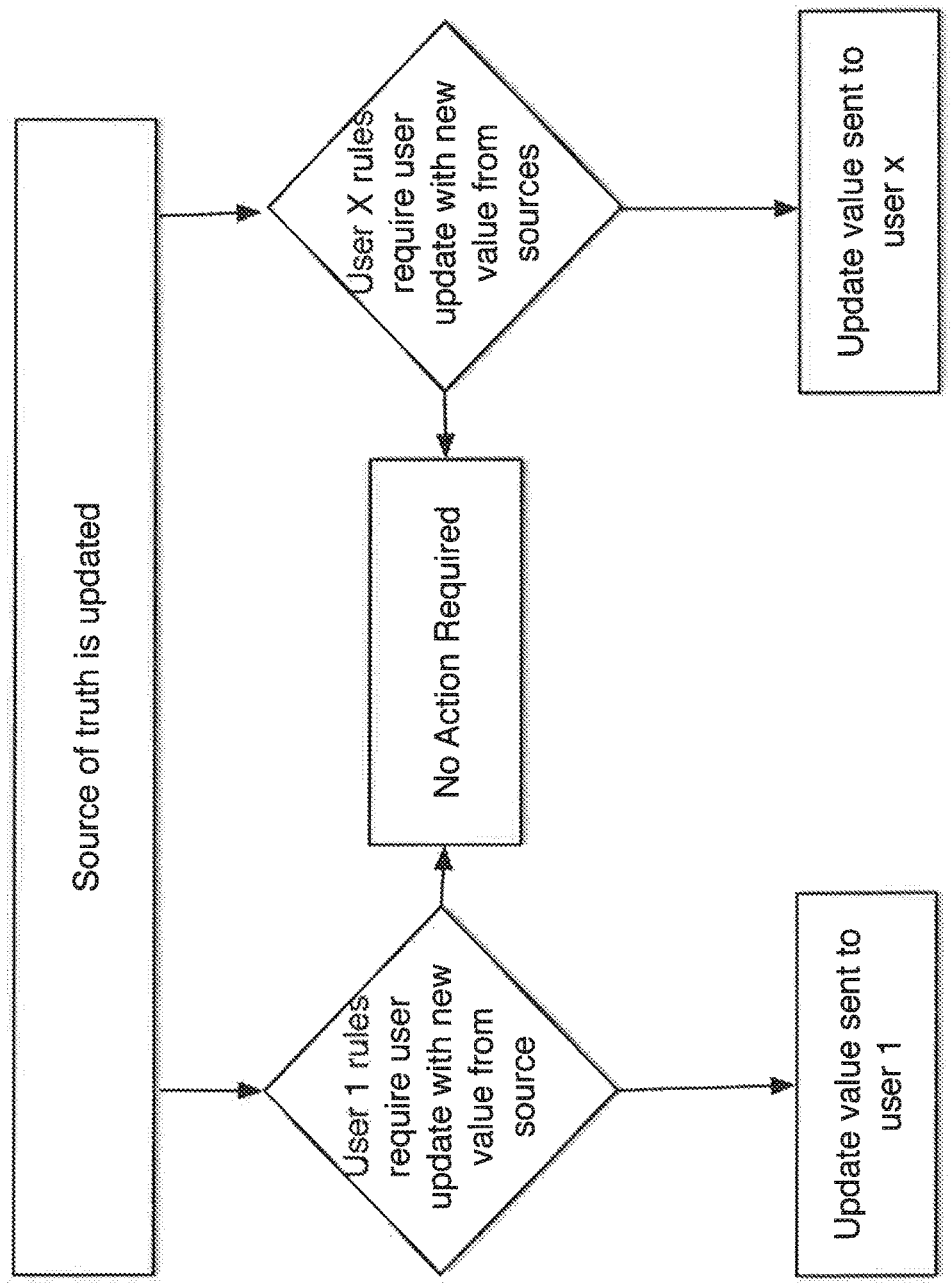
FIG. 6 illustrates the flow of a further decision support algorithm in accordance with the present invention which provides a source of truth synchronization.

As seen in FIG. 6, the identified source of truth may change over time as new information is gained. The specific User rules define the conditions that define when the specific User system is updated with the parameter value. The rules may vary depending on the specific user system. Examples of truth of source are identified in the following examples.
Drug Cost:

The actual cost of drugs is a critical parameter utilized in several systems within the hospital. The systems utilizing the drug cost include: Purchasing, Pharmacy, Drug Dispensing Cabinets, and Billing. The Purchasing system is required to have the actual cost of a drug for each purchase order. Therefore, Purchasing is the identified Source of Truth.

The Pharmacy maintains an accurate inventory by lot number. Therefore, utilizing the agnostic communication system the most accurate drug cost would be determined by when the Pharmacy system requesting the price of the drug for a new lot from the Purchasing system. Examples of options maybe when the lot is received by Pharmacy in one system, and when the lot is first dispensed in another. Depending on the Pharmacy system utilized, the business rule would be defined when the Pharmacy system obtains the drug cost from the Purchasing system.
Patient Vital Signs Paper System:

If manual paper records are used the official source of the patient vital signs is what the medical practitioner recorded. However, the most accurate value at the time of arrival is the value initially displayed by the medical device. With the agnostic electronic system, the patient records are automatically populated with the vital signs from the medical designs as soon as these patient is attached to each machine.
Patient Drug Delivery:

Medical practitioner records what they programmed an infusion pump to deliver for each drug. This value is not based on the actual programming of the infusion pump. The most accurate programming record is retrieved from the infusion pump as the programming is completed and drug delivery initiated. This approach also ensures that every user interaction with the infusion pump is recorded in the patient record.

Figure 7:
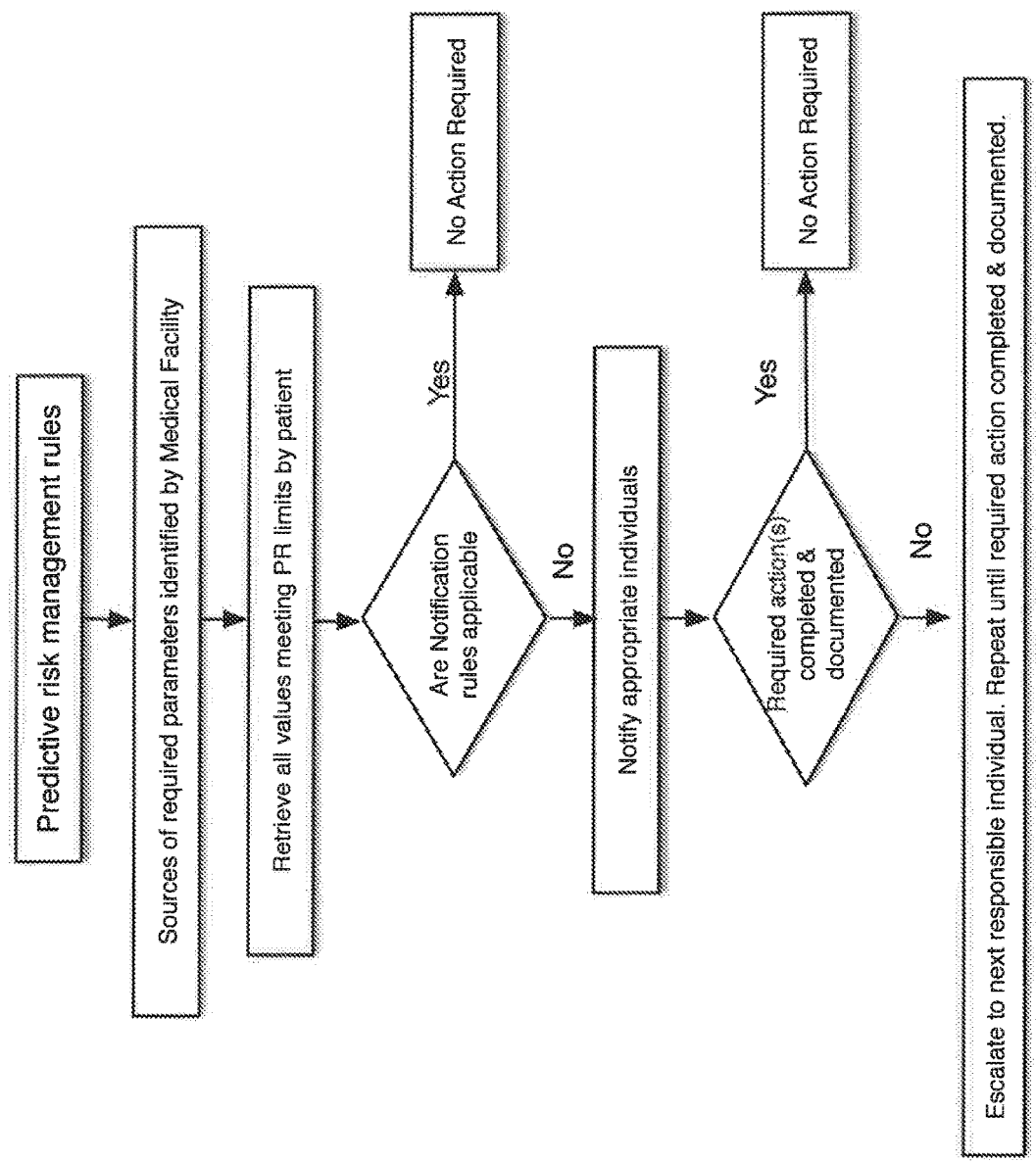
FIG. 7 illustrates the flow of a further decision support algorithm in accordance with the present invention which involves the predictive risk management tools of the present invention.

FIG. 7 illustrates a rules engine for use in the predictive risk management tool of the present invention. One example of a predictive risk management tools is the Sepsis Monitoring tool. Sepsis is one of the most serious patient acquired complications in medical facilities. The response time to a sepsis alert is well defined. However, ensuring the notification of all responsible individuals, required to respond as quickly as 10 minutes, is complicated at best. Although several existing systems may ensure that all notifications were sent and received, the present invention is an improvement over the existing systems, in that the system tracks response time and when necessary escalates the notification to an alternate responsible individual providing an additional safety nets to ensure that required treatment takes place within required time limits. The critical significance of response times to Sepsis alerts has been well documented. Delays in response times increase the probability of patient death.

Medical facilities utilize some form of a Sepsis monitoring and response system. The monitoring system defines potential sepsis predictors and their values. When any sepsis predictor is applicable to a specific patient the patient's sepsis monitoring record is updated. The sepsis-monitoring tool defines when medical observation and/or assessment is required. The medical practitioner responsible for the activity is notified immediately. If the required activity is not completed and documented within the specified time, the notification is escalated to the next identified individual. The sepsis-monitoring tool defines when the Sepsis Alert Team must take action. Each team member has specific assignments that must be accomplished within specified times. When the sepsis alert is triggered, the system immediately notifies each sepsis alert team member of his or her required assignment. If any required action is not completed within the specified time. The notification is escalated to the next identified responsible person for that action.

Process control principles require facts. Facts are often substantially different from the commonly accepted assumptions. Until the all-relevant facts are identified the optimization of any process is not complete. Often the assumed truths are the biggest hindrance to knowledge gain. One skilled in the art will understand that the significance of a system capable of collecting any number of variables to assess, without requiring all of them to be collected at the same time. As an example of new knowledge being gained, when ER nurses record vital signs of new patient, these recorded vital signs are used to determine the course of the patient's treatment. If the initial vital sign value was significantly different than the recorded value, then it will be necessary to resolve the difference.

For example, if an initial SpO2 value was 83% when the patient was connected to the SpO2 monitor, and when manually recorded the SpO2 value was 97%, the difference is not the nurse's accuracy. The difference is due to the time between the recordings and the fact that the initial machine value was before the patient received 100% oxygen for approximately 3 minutes before the manual recording. The patient will be at risk if the physician orders a stress test of the heart. No one is to blame, treating nurse's primary roles is to treat the patient immediately to stabilize patient. Step 1 put on oxygen, step 2 attach to the monitor, step 3 check pulse rate and so on until all treatments are complete, documenting the SpO2 value may not be seen as a time critical issue. In this discussion, the patient records presented the Physician with assumed facts indicated that the patient's symptoms would most accurately be assessed with a cardiac stress test. However, the data from the SpO2 monitor when initially connected to the patient indicated that the evaluation should more appropriately focusing on the potential of a pulmonary emboli. This example provides both an understanding of the significance of fact-based decisions. In this case, the patient monitor was the source of truth for the SpO2 value, not the recorded value. Automated data collection from the monitor was not available in this case. The example points out the critical need for accurate patient records in determining the correct course of treatment. This is an example of a real event experienced by one of the inventors. One skilled in the art will understand how to utilize the infrastructure described here to utilize the infrastructure to provide a means to facilitate the medical practitioners gain new knowledge to make improvements to their processes.

One skilled in the art will understand how to utilize the infrastructure described here to provide a means to facilitate the medical practitioners, gaining new knowledge, to make improvements to their processes. One skilled in the art also understands the significance of utilizing any parameter (data value) used in more than one SFSS or record requires that the value is consistently the same in all locations where it is used. One skilled in the art will also understand how to identify the true source of truth or to develop a plan to identify the source of truth. One skilled in the art will also understand how to implement a process to achieve this requirement.

The Interoperability Environment allows the hospital to identify their recognized source of truth, the hospital also identifies where that parameter (data value) is also used. Once this information is communicated the Interoperability Environment has the capability to synchronize all the locations sharing that value. This is done for each parameter in multiple subsystems.

Once there are well defined and controlled processes established using factually based identified sources of truth with access to all physiological data relevant to the patient care, the vision of advancing interoperability to support Physiological Based Closed Loop Controlled Medical Devices truly begins. It is critical to note that Physiological Based Closed Loop Controlled Medical Devices using clinically proven algorisms is not the first step in the journey. This requires extensive clinical study to validate each algorithm. Prior to any meaningful clinical study being considered, the processes being discussed in this patent must be in place to collect and analyze all relevant data including patient outcomes and predictors of those outcomes.

The more appropriate starting point is caregiver directed patient care instructions supported by Advanced Clinical Guidances to ensure compliance with those instructions and protocols. These instructions define the starting therapy, frequency of monitoring specific physiological patient parameters, including patient monitoring devices as well as labs and medical practitioner observations, the upper and lower physiological parameter values that determine when to increase and decrease therapy parameters. The care giver directed patient care instructions provide all the information required to establish and define the workflow with specific details sufficient to establish required scheduling times for monitoring, testing and evaluations schedules and required responses. The limits and actions required based on physiological parameters are defined for the specific patient. All physiological responses of the patient are reported by the originating source of truth for each physiological response. The entirety of the information managed by the Interoperability Environment, regarding this caregiver directed patient care instruction is the equivalent of any other workflow condition. The exception being that the caregiver provided patient care instruction is specifically defined for the patient based on the patient's current conditions. One skilled in the art can readily see how to leverage the capabilities of the global Interoperability Environment to deliver the care giver directed patient care instructions in an almost, if not, fully automatic manner with 2-way communication being utilized to program the medical device at appropriate points identified in the care giver directed patient care instructions. One skilled in the art can see that the invention provides the means to accomplish Physiological Based Closed Loop System Controlled Medical Devices based on evidence collected using Care giver directed patient care instructions.

Example 1

An Admission Discharge and Transfer System (or ADT) is used to schedule surgeries in the operating rooms. Once the patient is identified and recorded in the system, the system accesses the ADT to confirm the patient is scheduled and compatible with the ADT record.

To verify the patient is the correct patient for the case, several items must be compared between the ADT record and the patient identification (ID) band. These include: patient name and patient number. Additionally, information from the ADT and patient ID will be utilized to populate the anesthesia record, including: case number, patient name, patient number, assigned anesthesiologist, attending surgeon, type of protocol, etc.

Patient history from the Electronic Medical Record (EMR) is required to be documented in the anesthesia record. Therefore, the system obtains the required information from the EMR and populates the anesthesia record with the required information. Vital signs from a medical device are required to be recorded at specified time frames in the anesthesia record. The system obtains the vital signs from the medical device and sends the required information into the patient record(s). This could be the anesthesia record and the Electronic Medical Record system at the same time.

More detailed listing of information pulled from the EMR to populate the anesthesia record include: Patient name and number, relevant patient history such as allergies, heart condition, known physiological conditions which may increase the complexity of the procedure or impact the care of the patient.

Key patient data collected during the procedure must be sent to the EMR and entered into the appropriate location to ensure that the values are accurately recorded as part of the case. Examples include: attending practitioner, specific practitioner responsible for performing a specific activity during the case, vital signs collected from the active patient monitors, manually enter values as required by the procedure protocol.

The information from the anesthesia record including, drugs delivered, disposable medical devices, services provided, level of medical practitioner charged for the service, etc. are pushed to the billing system to generate accurate and timely billing. This information must be accurately sent to the billing system in a manner that ensures all required information is assigned to the correct patient, case, as well as other appropriate devices and records.

Thus, every connected medical device interacts with the medical device data system (MDDS) and the status of the medical device may be monitored remotely. Medical practitioners are allowed to create workflow screens to document and communicate the desired patient therapy planned.

As new or different sensors are identified and/or developed, the workflow screens support the collection of the new required data. This is accomplished using the system of the present invention and in accordance with the algorithms employed. The status of any Medical Device may be monitored remotely.

Further, medical device operational history can be collected proactively to support failure investigation of any potential safety event. Remote monitoring by supervision is enhanced. Physicians may remotely review the status of their patients. The system of the present invention allows the medical device(s) to provide the patient status with all sensors identified available for the physician to review. Further, medical practitioners may remotely adjust the instructions in response to patient response to treatment.

Example 2

Background

Sepsis is a major complication associated with patient care in hospitals. The total impact on family members and total cost of patient care is enormous. The issue is so large that there are US and International guidelines and initiatives to address the early identification of sepsis. The need for early identification is routinely seen as being as close to time zero of the infection starting as possible. Therefore, there is a need to initiate treatment as soon as possible. Additionally, there is a need to bundle a series of treatment protocols and patient evaluations to most effectively address sepsis effectively. The collection of the data required to predict sepsis as soon as possible also supports the early detection of other potentially less aggressive infections such as pneumonia and urinary tract infections since both of these may be a result of sepsis as well as other causes. The clinical practice guidelines for the management of sepsis are provided by the International Guidelines for Management of Severe Sepsis and Septic Shock (2012).

The information required to identify potential Sepsis complications is routinely entered into various patient records and generated by medical devices. However, there is not a tool that readily consolidates the various sources of information into the Sepsis Screening Checklist. The checklist is utilized to identify when the Sepsis care protocol starts. Any tool that decreases the delay between have the required information and the start of the Sepsis care decreases negative patient outcomes. Also, the Sepsis care bundles have specified time limits for required activities.

The Present Invention

The present invention provides a system which includes an engine and support tools provide a platform to leverage the review of active patient records to identify patients with indications common to sepsis symptoms. The present invention has the capability to collect the required data, populate sepsis assessment checklists and then identify any checklist that meets hospital guidelines for elevated patient evaluation.

All Sepsis Screen Checklists require collection of data from multiple sources. Remote review has the potential to decrease the time between the patient record being updated and the provider reviewing the updated patient condition. Therefore, the product could be offered as a quality and resource management tool designed to improve timeliness of required responses with the use of prompts/notification based on hospital defined criteria.

The present invention uses the following steps:
The Hospital's Sepsis Screening Checklist format, is populated, using the Hospital's format, as the information is received from identified sources.
The patient initial evaluation is entered into the Sepsis Screening Checklist.
The patient care outcome data listed on the sepsis checklist are pulled into the data base as available.
The patient physiological conditions as reported by medical devices, lab reports, and the like, are pulled into the Sepsis Screening Checklist.

A review is made to update patient records against the Sepsis Screening Checklist and corresponding hospital defined criteria prompts.

Remote view updates become based on the latest update to the patient's Sepsis Screening Checklist:

Dynamic dashboard screens utilized by Infection control and remote support (lab, pharmacy, physicians, etc.) are updated when appropriate.

Static dashboard screens utilized in the patient's care area are updated when appropriate.

Any identified notifications are initiated.

A remote view will be able to provide access to the patient specific Sepsis Screening Checklist to support timely access to the information required by the provider to determine appropriate action.

Utilizing the hospital Sepsis Bundle protocols, the remote view will provide prompts to remind provides of when protocol specific activities are scheduled. Defined time periods can be, for example, 5 minutes, 15 minutes, or 60 minutes.

The Sepsis Screening Checklist will be populated as the data is available. Data sources include but are not limited to employee healthcare records (or HER), lab results, and/or physiological data from medical devices.

Care area dashboards can visually display when updated patient's Sepsis Screening Checklist indicates that hospital defined criteria require review. The dashboard is not intended to replace the normal review process of the provider since it is intended as a support tool to assist in the notification that new information has been received since the last review. Remote dashboards also may be established for various members of the care team that participate in the sepsis response process, such as sepsis response team, infection control, pharmacy lab, and/or the responsible physician, but the dashboards are not replacements for the hospital required notification process. Notification protocols may be supported with the present invention, and the desired notifications to be sent based on hospital defined levels of notifications. Sepsis care protocols may be supported with prompts to improve the compliance with the prescribed activities and specified times.

Similar quality, process control and resource management tools may be employed as add-on features to the present invention. The elements for a sepsis remote view system would include, for example, the following:

A data repository, which could include language translation drivers when ECO system drivers are utilized, a report writer module, a guidance engine, an interface module, an encounter management module, including a table configured for specific remote view tools definitions of how to handle specific types of encounters and what to do with the data, a module which provides patient association, such as which patient is in which bed, and provider association, such as which provider is associated with which encounter (such as, in care unit and in other locations), a dynamic dashboard to facilitate management of Infection control, which could include notification tools.

When the patient arrives at the hospital, the base information will be recorded, such as, any infection will be identified at arrival, and any new infection or suspected infection noted in patient history. Any of the SIRS identifiers will be entered based upon customer defined prompts, such as temperature, including any assigned limit, heart rate, respiratory rate, U/O, SBP, MAP, increases in $O_2$ or increases in required labs, such as WBC, blood glucose, or $SaO_2$. The system will then generate a sepsis bundle of information, including the time of sepsis alert, a sepsis order, including time received, ordering Dr., labs, lab draw time, lab results, including lactate, WBC, blood Culture, blood glucose, and generate information regarding the fluid bolus, such as fluid ID, Bolus programmed, any follow fluids, antibiotics ordered & time, pharmacy notification if required, antibiotics delivered, SBP Value, and MAP Value.

Based upon the information gathered and imputed, the actions required will be generated, including, within 5 minutes, a notice will be sent to the Sepsis response team an activate Sepsis alert will be generated, the doctor will be notified to initiate a Sepsis order bundle. Within 10 minutes, a prompt will be issues that order has not been received. Within 15 minutes, the Lab will draw for STAT Lactate level and Blood Cultures×2, and obtain antibiotics, if not available notify Pharmacy for STAT delivery. Within 60 Minutes, Broad Spectrum IV antibiotics are administered after the cultures are drawn, according to the following protocol:

STEP A: In the presence of SBP<90, MAP<65 or drop in SBP>40 pts from last normal, OR lactate >4, STEP B: Give a RAPID infusion bolus of 30 ml/kg (normal saline or lactated ringers)

STEP C: Measure weight in kg _____×30=ml of fluid (chart both start and stop times)

If initial lactate level is >2, draw a repeat lactate level within 4 hours of positive sepsis screen. (lactate order will be reflexed automatically)

If hypotension persists after 30 ml/kg bolus, or lactate≥4=Septic Shock Time

STEP D: Start IV vasopressors for persistent hypotension.

STEP E: Provider to perform focused exam within 4 hours of Septic Shock time.

Although the invention has been described in detail with reference to particular examples and embodiments, the examples and embodiments contained herein are merely illustrative and are not an exhaustive list. Variations and modifications of the present invention will readily occur to those skilled in the art. The present invention includes all such modifications and equivalents. The claims alone are intended to set forth the limits of the present invention.

What we claim is:

1. An Interoperability Environment telecommunication network comprising:

a telecommunications network;

an Eco System module, compatible with commonly used operating systems, including communication and storage rules providing a means to act as a communication conduit for two-way collecting and storing electronic data from at least one electronic device including medical devices, and translating the received electronic data into the appropriate format required by the receiving electronic target including medical devices and data translation means for translating the received electronic data into the appropriate format required by one or more the receiving electronic targets, via one or more communication vehicles;

a software core engine comprised of a data management module including communications rules providing the means to agnostically receive data from an unlimited number of electronic device sources, a means to agnostically send data electronically to an unlimited number of electronic targets;

a data storage rules engine providing a means for time stamping of data including linking to the appropriate report formats used at the time of data collection, and a means of supporting the addition and deletion of parameters whereby rules may be added and deleted multiple times;

a guidance engine comprising a means to manage the requirements of one or more specific protocol workflows, a means to manage the requirements of any care area workflows, a means to manage the monitoring and response to management requirements including of one or more advanced clinical guidance process control limits and response to scheduled or required activities and required documentation, as well as prompts, alerts, notifications and escalation of notifications; and a source of truth rules engine comprising a means to identify when a parameter, shared by more than one electronic systems, is changed, and once changed, provide means to update the parameter in each connected electronic system with the new value, and means to defer the update of the parameter based on defined rules when applicable.

2. The Interoperability Environment telecommunication network of claim 1, wherein the Data Management module has no predetermined documentation format or field population required to function properly, allows any portion of the universe including protocols, required documentation, guidance, or workflows be changed without losing any functionality of the Interoperability Environment.

3. The Interoperability Environment telecommunication network of claim 1, wherein the accuracy of information is either provided by the formally recognized source of truth or is provided by a system that is in validated agreement with the source of truth.

4. The Interoperability Environment telecommunication network of claim 1, wherein one or more advanced clinical guidance, defined by the hospital, regulatory agency, accreditation organization, may be populated in near real time to ensure timely notification of the new patient information is available, when hospital alert or action limits are met to initiate notification and/or formal tracking of response times of required actions.

5. The Interoperability Environment telecommunication network of claim 1, wherein routine or medical practitioner ordered activities are monitored and tracked, and when appropriate notification prompts are issued to responsible individuals.

6. The Interoperability Environment telecommunication network of claim 1, wherein all identified patient care information is stored separately from, all identified quality/process control data stored separately.

7. The Interoperability Environment telecommunication network of claim 1, wherein the network supports one or more actions that result in changes the hospital infrastructure, including medical device models, electronic medical records, electronic medication administration record, laboratory, Blood Bank, drug dispensing platform, Pharmacy management system, Purchasing.

8. The Interoperability Environment telecommunication network of claim 1, including providing support of the utilization of advanced process control tools and Artificial Intelligence tools to deliver a spiral of improvement of patient care based on fact based recognized source of truth alignment across the hospital record systems including medical devices.

9. The Interoperability Environment telecommunication network of claim 1, including providing means to accelerate the response times of responsible individuals when hospital defined conditions require initiation of timely response to ensure patient outcome is optimized, utilizing notification, response tracking tools, and escalation notification as defined by the hospital.

10. The Interoperability Environment telecommunication network of claim 1, wherein the system eliminates the silo effect of stand-alone Specially Focused Software Systems by linking common parameter values to the officially recognized source of truth rather than allowing each to see itself as the source of truth.

11. The Interoperability Environment telecommunication network of claim 1, designed to support the tools required to utilize an electronic device connectivity device wherein the communication may be two-way with the Interoperability Environment providing updates and/or instructions to the appropriate electronic device(s) including medical devices.

12. The Interoperability Environment telecommunication network of claim 1, including providing a means to provide two-way communication between one or more physiological data sources to compare identified physiological parameters to the most recent Physician (or an authorized medical practitioner) order and when all defined parameter conditions have been met update the next step in the therapy order being implemented by the medical device(s) providing the therapy.

13. The Interoperability Environment telecommunication network of claim 1, wherein the truth configuration engine comprises an algorithm.

14. The Interoperability Environment telecommunication network of claim 1, wherein the accuracy of information is either provided by the formally recognized source of truth or is provided by a system that is in validated agreement with the source of truth.

15. The Interoperability Environment telecommunication network of claim 1, wherein one or more advanced clinical guidance, defined by the hospital, regulatory agency, accreditation organization, may be populated in near real time to ensure timely notification of the new patient information is available, when hospital alert or action limits are met to initiate notification and/or formal tracking of response times of required actions.

16. The Interoperability Environment telecommunication network of claim 1, wherein the updated parameters may be populated in near real time to ensure timely notification of the new patient information is available, when hospital alert or action limits are met to initiate notification and/or formal tracking of response times of required actions.

17. The Interoperability Environment telecommunication network of claim 1, further including at least one monitoring station comprising monitoring equipment wherein the monitoring equipment comprises instructions for monitoring data elements and for sending the monitored data elements an interoperability environment engine via the telecommunications network, wherein the interoperability environment engine comprises instructions for receiving monitored data elements from patients and accessing patient data elements indicative of a medical conditions associated with each of the patients.

18. The Interoperability Environment telecommunication network of claim 1, further including a patient database containing information concerning the medical condition, history, and status of each of the patients.

19. A process of providing an officially recognized source of truth for patients, hospitals, and healthcare clinics comprising the steps of providing an Interoperability Environment telecommunication network comprising:

a telecommunications network;

an Eco System module, compatible with commonly used operating systems, including communication and storage rules providing a means to act as a communication conduit for two-way collecting and storing electronic data from at least one electronic device including medical devices, and translating the received electronic data into the appropriate format required by the receiving electronic target including medical devices and data translation means for translating the received electronic data into the appropriate format required by one or more the receiving electronic targets, via one or more communication vehicles;

a software core engine comprised of a data management module including communications rules providing the means to agnostically receive data from an unlimited number of electronic device sources, a means to agnostically send data electronically to an unlimited number of electronic targets;

a data storage rules engine providing a means for time stamping of data including linking to the appropriate report formats used at the time of data collection, and a means of supporting the addition and deletion of parameters whereby rules may be added and deleted multiple times;

a guidance engine comprising a means to manage the requirements of one or more specific protocol workflows, a means to manage the requirements of any care area workflows, a means to manage the monitoring and response to management requirements including of one or more advanced clinical guidance process control limits and response to scheduled or required activities and required documentation, as well as prompts, alerts, notifications and escalation of notifications; and a source of truth rules engine comprising a means to identify when a parameter, shared by more than one electronic systems, is changed, and once changed, provide means to update the parameter in each connected electronic system with the new value, and means to defer the update of the parameter based on defined rules when applicable, whereby hospitals and healthcare facilities can establish a continuous spiral of improved patient care outcomes and regulatory compliance.

\* \* \* \* \*